United States Patent
Viola (10) Patent No.: US 8,028,882 B2
(45) Date of Patent: Oct. 4, 2011

(54) ANVIL POSITION DETECTOR FOR A SURGICAL STAPLER

(75) Inventor: Frank Viola, Sandy Hook, CT (US)

(73) Assignee: Tyco Healthcare Group, North Haven, CT (US)

( * ) Notice: Subject to any disclaimer, the term of this patent is extended or adjusted under 35 U.S.C. 154(b) by 0 days.

(21) Appl. No.: 11/799,687

(22) Filed: May 1, 2007

(65) Prior Publication Data

US 2008/0272171 A1  Nov. 6, 2008

(51) Int. Cl.
*A61B 17/115* (2006.01)

(52) U.S. Cl. ............... 227/175.1; 227/180.1; 227/181.1; 227/19

(58) Field of Classification Search ............... 227/175.1, 227/175.2, 180.1, 181.1, 19
See application file for complete search history.

(56) References Cited

U.S. PATENT DOCUMENTS

| | | | |
|---|---|---|---|
| 4,598,579 A | 7/1986 | Cummings et al. | |
| 4,601,724 A | 7/1986 | Hooven et al. | |
| 5,358,506 A * | 10/1994 | Green et al. | 606/151 |
| 5,383,880 A | 1/1995 | Hooven | |
| 5,433,721 A | 7/1995 | Hooven et al. | |
| 5,464,144 A * | 11/1995 | Guy et al. | 227/176.1 |
| 5,518,163 A | 5/1996 | Hooven | |
| 5,518,164 A | 5/1996 | Hooven | |
| 5,667,517 A | 9/1997 | Hooven | |
| 5,766,166 A | 6/1998 | Hooven | |
| 5,779,131 A * | 7/1998 | Knodel et al. | 227/176.1 |
| 5,814,044 A | 9/1998 | Hooven | |
| 5,817,013 A | 10/1998 | Ginn et al. | |
| 5,865,361 A * | 2/1999 | Milliman et al. | 227/176.1 |
| 5,891,140 A | 4/1999 | Ginn et al. | |
| 5,951,549 A | 9/1999 | Richardson et al. | |
| 5,957,884 A | 9/1999 | Hooven | |
| 6,007,512 A | 12/1999 | Hooven | |
| 6,022,313 A | 2/2000 | Ginn et al. | |
| 6,036,681 A | 3/2000 | Hooven | |
| 6,086,586 A | 7/2000 | Hooven | |
| 6,113,596 A | 9/2000 | Hooven et al. | |
| 6,179,837 B1 | 1/2001 | Hooven | |
| 6,264,087 B1 | 7/2001 | Whitman | |
| 6,315,184 B1 | 11/2001 | Whitman | |
| 6,348,061 B1 | 2/2002 | Whitman | |
| 6,350,264 B1 | 2/2002 | Hooven | |
| 6,391,029 B1 | 5/2002 | Hooven et al. | |

(Continued)

FOREIGN PATENT DOCUMENTS

DE  19951940 C2 * 11/2001

(Continued)

OTHER PUBLICATIONS

European Search Report for EP 08251574.3-2310 date of completion is Aug. 5, 2005 (3 pages).

*Primary Examiner* — Sameh H. Tawfik
*Assistant Examiner* — Michelle Lopez (57) ABSTRACT

An anvil position detector is provided for use with a surgical stapling instrument. The anvil position detector includes a projection formed on a driving or jaw closure mechanism of the surgical instrument and a recess for a notch formed on the jaw or anvil of the surgical instrument. Engagement of the projection with the notch provides a tactile and/or audible indication to the operator of the surgical instrument that the anvil or jaw is in proper alignment with the remainder of the surgical instrument.

19 Claims, 6 Drawing Sheets

U.S. PATENT DOCUMENTS

| | | | |
|---|---|---|---|
| 6,443,973 B1 | 9/2002 | Whitman | |
| 6,464,701 B1 | 10/2002 | Hooven et al. | |
| 6,488,197 B1 | 12/2002 | Whitman | |
| 6,491,201 B1 | 12/2002 | Whitman | |
| 6,505,768 B2 | 1/2003 | Whitman | |
| 6,517,565 B1 | 2/2003 | Whitman et al. | |
| 6,533,157 B1 | 3/2003 | Whitman | |
| 6,681,979 B2 | 1/2004 | Whitman | |
| 6,695,199 B2 | 2/2004 | Whitman | |
| 6,698,643 B2 | 3/2004 | Whitman | |
| 6,716,230 B2 | 4/2004 | Whitman | |
| 6,716,232 B1 * | 4/2004 | Vidal et al. | 606/205 |
| 6,716,233 B1 | 4/2004 | Whitman | |
| 6,793,652 B1 | 9/2004 | Whitman et al. | |
| 6,843,403 B2 | 1/2005 | Whitman | |
| 6,846,307 B2 | 1/2005 | Whitman et al. | |
| 6,846,308 B2 | 1/2005 | Whitman et al. | |
| 6,846,309 B2 | 1/2005 | Whitman et al. | |
| 6,849,071 B2 | 2/2005 | Whitman et al. | |
| 6,981,941 B2 | 1/2006 | Whitman et al. | |
| 7,032,798 B2 | 4/2006 | Whitman et al. | |
| 7,077,856 B2 | 7/2006 | Whitman | |
| 7,114,642 B2 | 10/2006 | Whitman | |
| 7,238,145 B2 * | 7/2007 | Robbins et al. | 482/11 |
| 7,300,444 B1 * | 11/2007 | Nielsen et al. | 606/153 |
| 2001/0031975 A1 | 10/2001 | Whitman et al. | |
| 2001/0045442 A1 | 11/2001 | Whitman | |
| 2002/0049454 A1 | 4/2002 | Whitman et al. | |
| 2002/0052623 A1 | 5/2002 | Whitman | |
| 2002/0084304 A1 | 7/2002 | Whitman | |
| 2002/0165444 A1 | 11/2002 | Whitman | |
| 2002/0165541 A1 | 11/2002 | Whitman | |
| 2002/0198554 A1 | 12/2002 | Whitman et al. | |
| 2003/0009154 A1 | 1/2003 | Whitman | |
| 2003/0050628 A1 | 3/2003 | Whitman et al. | |
| 2003/0050654 A1 | 3/2003 | Whitman et al. | |
| 2003/0055411 A1 | 3/2003 | Whitman et al. | |
| 2003/0073981 A1 | 4/2003 | Whitman et al. | |
| 2003/0073982 A1 | 4/2003 | Whitman | |
| 2003/0089757 A1 | 5/2003 | Whitman | |
| 2003/0105478 A1 | 6/2003 | Whitman et al. | |
| 2003/0125717 A1 | 7/2003 | Whitman | |
| 2003/0130677 A1 | 7/2003 | Whitman et al. | |
| 2003/0132268 A1 | 7/2003 | Whitman | |
| 2003/0176794 A1 | 9/2003 | Whitman | |
| 2004/0068274 A1 | 4/2004 | Hooven | |
| 2004/0094597 A1 | 5/2004 | Whitman et al. | |
| 2004/0097958 A1 | 5/2004 | Whitman et al. | |
| 2004/0111012 A1 | 6/2004 | Whitman | |
| 2004/0111081 A1 | 6/2004 | Whitman et al. | |
| 2004/0149802 A1 | 8/2004 | Whitman | |
| 2004/0153124 A1 | 8/2004 | Whitman | |
| 2004/0249368 A1 | 12/2004 | Hooven | |
| 2005/0187534 A1 | 8/2005 | Wilson | |
| 2005/0187576 A1 | 8/2005 | Whitman et al. | |
| 2005/0192609 A1 | 9/2005 | Whitman et al. | |
| 2006/0020213 A1 | 1/2006 | Whitman et al. | |
| 2006/0089628 A1 | 4/2006 | Whitman | |
| 2006/0161149 A1 | 7/2006 | Privitera et al. | |
| 2007/0023476 A1 | 2/2007 | Whitman et al. | |
| 2007/0023477 A1 | 2/2007 | Whitman et al. | |
| 2007/0055219 A1 | 3/2007 | Whitman et al. | |
| 2007/0055304 A1 | 3/2007 | Whitman | |
| 2007/0056932 A1 | 3/2007 | Whitman et al. | |
| 2007/0057014 A1 | 3/2007 | Whitman et al. | |
| 2007/0075116 A1 | 4/2007 | Whitman | |
| 2007/0185477 A1 | 8/2007 | Hooven | |

FOREIGN PATENT DOCUMENTS

| | | |
|---|---|---|
| EP | 0600173 A | 6/1994 |
| WO | WO 03/030743 A | 4/2003 |

* cited by examiner

ANVIL POSITION DETECTOR FOR A SURGICAL STAPLER

BACKGROUND

1. Technical Field

The present disclosure relates to a jaw position detector for use with a surgical instrument. More particularly, the present disclosure relates to an anvil position detector for use in a surgical stapling instrument.

2. Background of Related Art

Various surgical instruments are used in surgical procedures to grasp and manipulate tissue. These instruments may include devices having relatively movable jaw structures such as, for example, graspers, cutters, etc.

Other types of surgical instruments having movable jaw structure include surgical staplers. Surgical staplers typically incorporate a staple containing cartridge and an anvil member movably mounted relative to the staple containing cartridge. Tissue is captured between the anvil member and the staple containing cartridge and the stapler is actuated to place one or more rows of staples through the captured tissue and, in some cases, cut the tissue between the rows of staples. In order to properly staple the tissue, it is often necessary that the anvil be moved to a predetermined position relative to the remainder of the surgical stapler and, in particular, relative to the elongate member upon which the anvil is mounted.

In specific instances, it is desirable to orient the anvil member relative to an elongate member of the surgical instrument such that a longitudinal axis of the anvil member is substantially parallel to a longitudinal axis of the elongate member. This may be necessary to ensure that staple pockets associated with the anvil member are in a proper position to fully crimp the staples closed about the tissue being stapled. When performing a procedure endoscopically, it is often difficult to tell when the longitudinal axis of the anvil member is in proper alignment with respect to the longitudinal axis of the elongate member.

Thus, it would be desirable to provide a surgical instrument having an indicator mechanism capable of ensuring proper alignment of a jaw or anvil of the surgical instrument with the remainder of the surgical instrument. It would be further desirable to provide an indicator mechanism which provides a tactile indication of the proper alignment. It would still further be desirable to provide an indicator mechanism which provides an audible indication of the proper alignment.

SUMMARY

There is disclosed a surgical instrument incorporating a jaw position detector. The surgical instrument generally includes a handle and a support or elongate member extending distally from handle. The elongate member defines a first longitudinal axis. A jaw assembly is mounted on a distal end of the elongate member and includes a staple cartridge and a movable jaw or anvil mounted relative to the staple cartridge. The anvil defines a second longitudinal axis. A drive mechanism is provided to move the anvil between an open position spaced apart from the staple cartridge to a closed position substantially adjacent the staple cartridge. A position detector is associated with the drive mechanism and the anvil such that position detector provides an indication to an operator of the surgical instrument when the first longitudinal axis is in substantial alignment with the second longitudinal axis. The drive mechanism includes a driver movable within the elongate tubular member.

The position detector includes a notch formed in the jaw and a projection on the driver engageable with the notch on the jaw. The notch is a transverse notch formed in the jaw and the projection on the driver is a cross pin oriented transverse to the driver. In one embodiment, engagement of the cross pin with the notch provides a tactile indication to the operator or user that the first longitudinal axis is in substantial alignment with the second longitudinal axis. In an alternative embodiment, engagement of the cross pin with the notch provides an audible indication to the operator or user that the first longitudinal axis is in substantial alignment with the second longitudinal axis.

There is also provided an alternative surgical instrument incorporating a jaw position detector. The surgical instrument includes a support member having a first longitudinal axis and a jaw movably mounted on the support member and having a second longitudinal axis. A drive mechanism is movable over the support member and operable to move the jaw are relative to the support member. A position detector is associated with the jaw and a drive mechanism such that the position detector provides an indication to an operator of the surgical instrument when the first longitudinal axis is in substantial alignment with the second longitudinal axis.

In one embodiment, the drive mechanism includes an outer tubular member movable over the support member and engageable with the jaw to move the jaw relative to the support member. The position detector includes a notch formed in the jaw and a projection in the outer tubular member. In one embodiment, the notch is a transverse notch formed in the jaw and the projection in the outer tubular member is an inwardly directed projection. In one embodiment, engagement of the projection with the notch provides a tactile indication to the user or operator. In an alternative embodiment, engagement of the projection with the notch provides an audible indication to the user or operator.

There is also disclosed an indicator for use with a jaw closure mechanism incorporating a threaded inner member and a threaded outer member. The indicator provides an indication to a user or operator when the threaded inner member is in a predetermined position relative to the threaded outer member. The position indicator includes a notch formed in the threaded inner member and a projection, engageable with the notch, formed in the threaded outer member. In one embodiment, engagement of the projection with the notch provides a tactile indication to the user or operator, while in an alternative embodiment, engagement of the projection with the notch provides an audible indication to the user or operator.

DESCRIPTION OF THE DRAWINGS

Various embodiments of the presently disclosed anvil position detector for use in a surgical stapler are disclosed herein with reference to the drawings, wherein.

DETAILED DESCRIPTION OF EMBODIMENTS

Embodiments of the presently disclosed anvil position detector for use in surgical staplers will now be described in detail with reference to the drawings wherein like numerals designate identical or corresponding elements in each of the several views. As is common in the art, the term "proximal" refers to that part or component closer to the user or operator, i.e. surgeon or physician, while the term "distal" refers to that part or component further away from the user.

Figure 1:
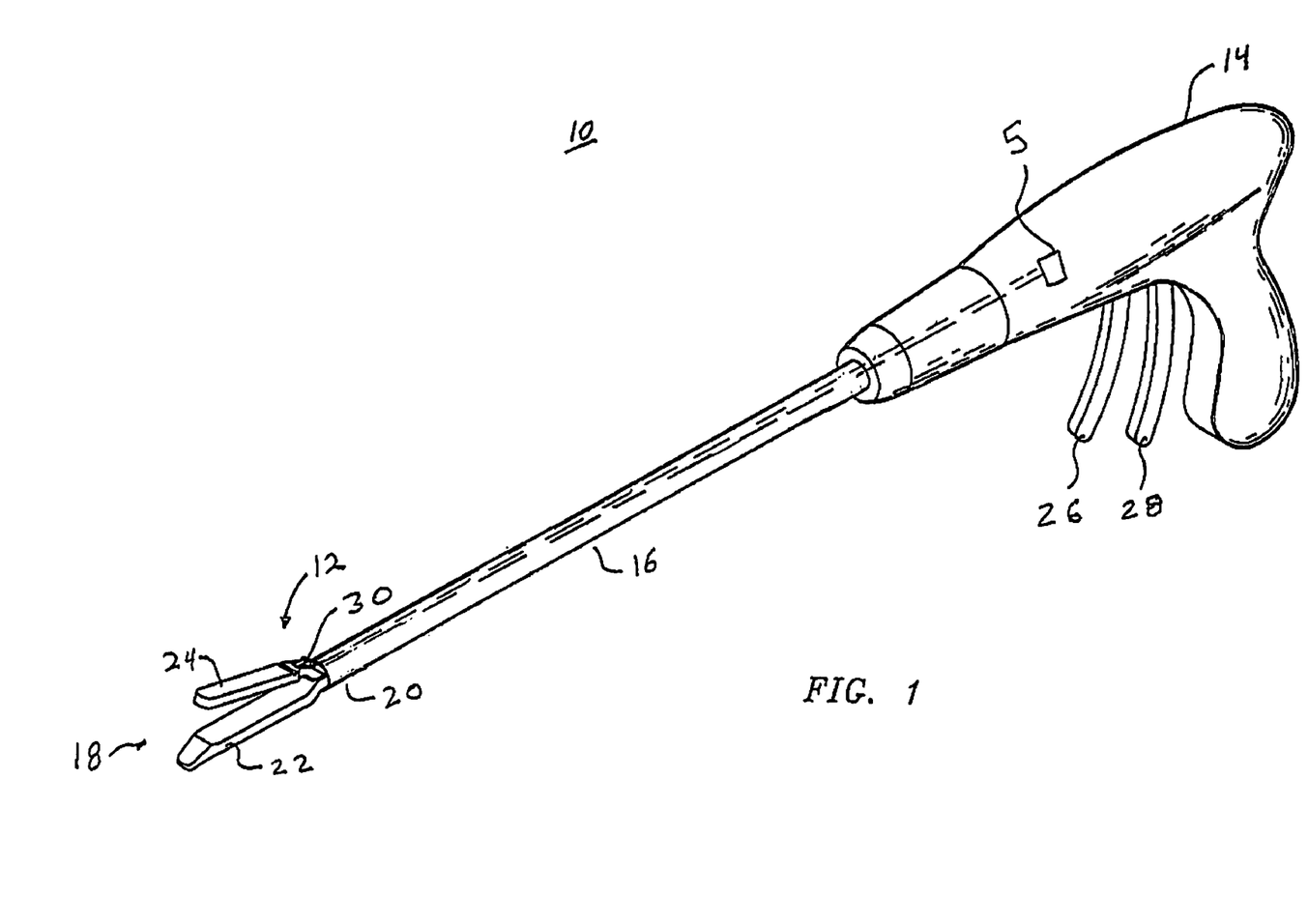
FIG. 1 is a perspective view of a surgical stapler incorporating one embodiment of an anvil position detector for use with a surgical stapler.

Referring to FIG. 1, there is illustrated as surgical stapler 10 incorporating one embodiment of an anvil position detector 12. Surgical stapler 10 is includes a handle 14 and an elongated tubular member 16 extending distally from handle 14. A jaw assembly 18 is provided on a distal end 20 of elongate tubular member 16. Jaw assembly 18 includes a staple cartridge 22 and an anvil 24 which is mounted for movement relative to staple cartridge 22. Staple cartridge 22 is of the type containing a plurality of staples (not shown) which are provided to be driven through tissue and into anvil 24 for crimping about the tissue. Staple cartridge 22 may be permanently mounted to elongate tubular member 16 or may be removable and therefore replaceable with a new staple cartridge 22. Anvil 24 is movable between an open position spaced apart from staple cartridge 22 to a closed position substantially adjacent staple cartridge 22.

Surgical stapler 10 additionally includes a first trigger 26 and a second trigger 28 movably mounted on handle 14. First trigger 26 is provided to move anvil 24 between the open and closed positions. Actuation of first trigger 26 operates to move a driver 30 longitudinally relative to elongate tubular member 16 so as to cam anvil 24 from the open position to the closed position. Actuation of second trigger 28 operates to eject staples from staple cartridge 22 through tissue and into anvil 24 for crimping about the tissue.

Figure 2:
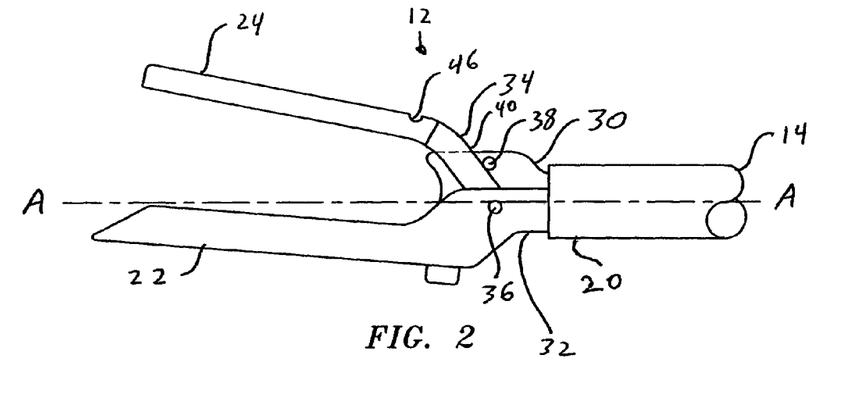
FIG. 2 is a side elevation view of the distal end of the surgical stapler of FIG. 1.

Referring now to FIG. 2, as noted above, staple cartridge 22 is mounted on elongate tubular member 14. Elongate tubular member 14 has a first longitudinal axis A-A. Specifically, a proximal end 32 is mounted to distal end 20 of elongate tubular member 14. A proximal end 32 of anvil 24 is movably mounted to proximal end 32 of staple cartridge 22 at pivot 36. In order to move anvil 24 between the open and closed positions, a cross pin 38 is provided on driver 30 and is engageable with an angled edge 40 at proximal end 34 of anvil 24. As cross pin 38 is driven against angled edge 40, anvil 24 is moved from the open to the closed position.

Figure 3:
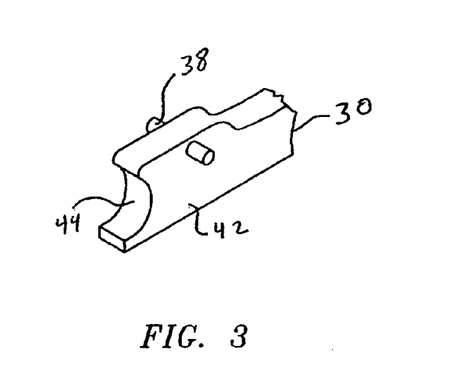
FIG. 3 is a perspective view of the distal end of a drive bar of the surgical stapler incorporating part of the anvil position detector.

Referring for the moment to FIG. 3, cross pin 38 is transversely mounted through a distal end of 42 of driver 30. Distal end 42 of driver 30 may additionally include an arcuate tissue stop 44 provided to prevent tissues from being pinched between anvil 24 and staple cartridge 22.

Referring back to FIG. 2, and as noted hereinabove, surgical stapler 10 includes anvil position detector 12 which is provided to give an indication to the operator of surgical stapler 10 when anvil 24 is in the proper position relative to elongate tubular member 14. Anvil position detector 12 includes a cross notch 46 formed in anvil 24 which cooperates with cross pin 38 on driver 30. Specifically, as anvil 24 is moved toward the closed position cross pin 38 moves toward and engages cross notch 46. When cross pin 38 engages cross notch 46, it does so in such a manner as to provide a tactile indication, such as the feeling of two parts snapping together, to the operator of surgical stapler 10. Additionally, the engagement of cross pin 38 with cross notch 46 may also provide an audible indication to the operator of surgical stapler 10 that cross pin 38 has engaged cross notch 46 and anvil 24 is properly oriented relative to elongate tubular member 14.

Figure 4:
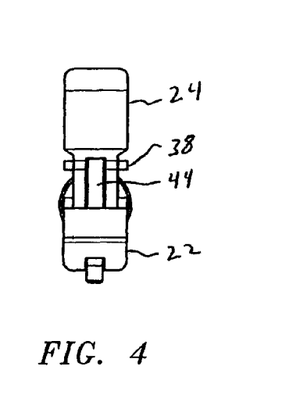
FIG. 4 is an end view of the distal end of the surgical stapler of FIG. 1.
Figure 5:
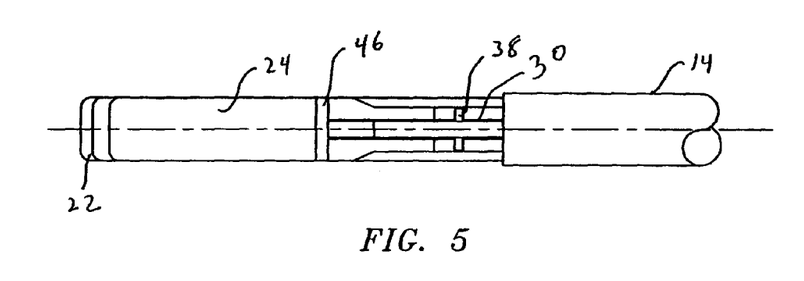
FIG. 5 is a top view of the distal end of the surgical stapler of FIG. 1.

Referring now to FIGS. 4 through 7, and initially with respect to FIGS. 4 and 5, in the initial position, anvil 24 is in the open position spaced apart from staple cartridge 22 and driver 30, containing cross pin 38, is in a proximal position relative to cross notch 46 in anvil 24.

Figure 6:
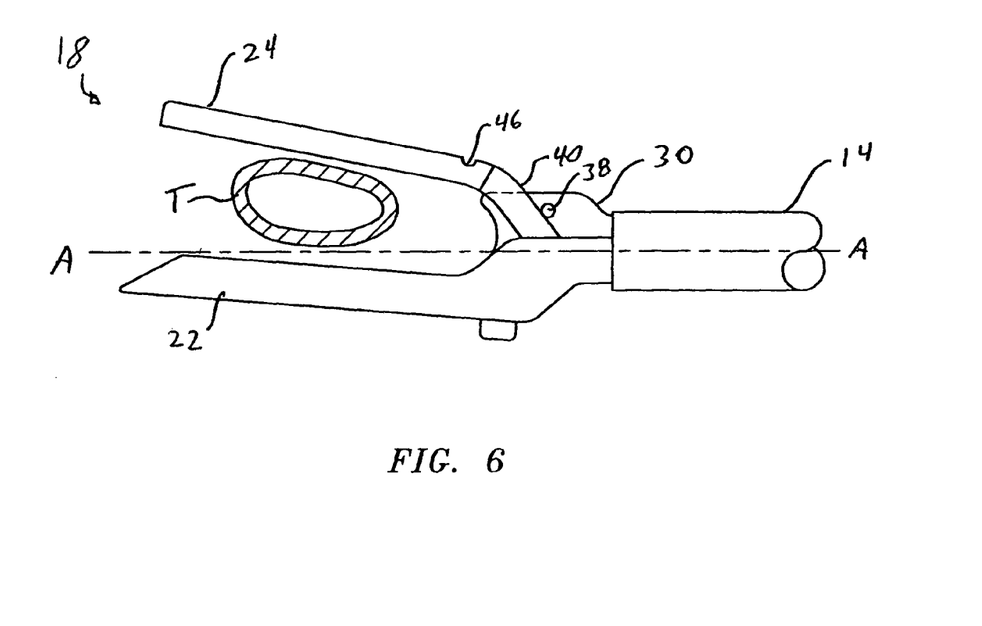
FIG. 6 is a side elevation view of the distal end of the surgical stapler of FIG. 1 positioned about tissue.
Figure 7:
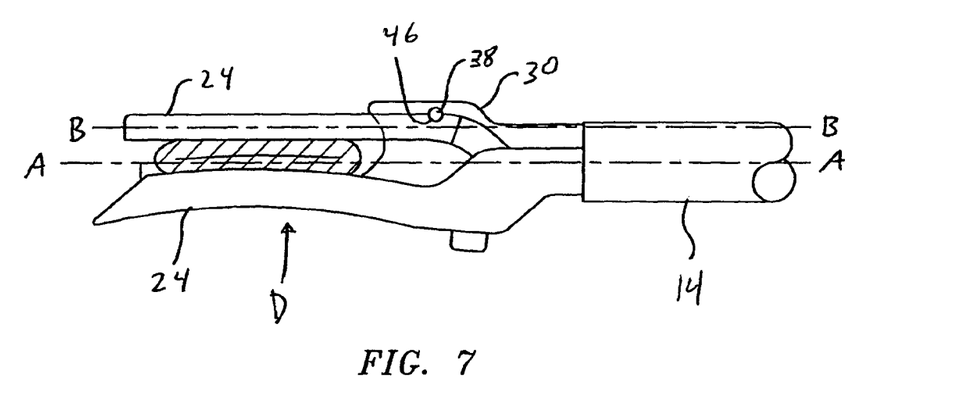
FIG. 7 is a side elevation view of the distal end of the surgical stapler of FIG. 1 with the tissue captured between the jaws and the anvil position detector engaged.

As best shown in the FIGS. 6 and 7, in use, jaw assembly 18 is positioned about a tubular tissue section T to be stapled. It should be noted that, while the discussion of anvil position detector 12 is being given relative to a surgical stapler 10 and an anvil 24, the operation of anvil position detector 12 is equally applicable to other surgical instruments having tissue engaging jaw structures such as, for example, graspers, cutters, etc. Once tissue T has been properly positioned within jaw assembly 18, first trigger 26 (FIG. 1) is actuated to move driver 30 distally relative to elongate tubular member 14. As driver 30 moves distally, cross pin 38 engages angled edge 40 of anvil 24 and cams anvil 24 to the closed position relative to staple cartridge 22.

It should be noted that the location of cross notch 46 is configured to correspond to the situation where a longitudinal axis B-B of anvil 24 is parallel to longitudinal axis A-A of elongate tubular member 14. Specifically, cross pin 38 engages cross notch 46 at the point where longitudinal axis B-B is parallel to longitudinal axis A-A of elongate tubular member 14. As cross pin 38 engages cross notch 46, cross pin 38 snaps into engagement with cross notch 46 giving both a tactile and audible indication to the operator of surgical stapler 10 that anvil 24 is in the proper orientation relative to elongate tubular member 14. Thus, cross pin 38, in combination with cross notch 46, forms an anvil position detector enabling the operator of surgical instrument 10 to be confident that the anvil 24 is in the proper position to crimps staples. As shown, staple cartridge 22 may undergo a certain amount of deflection D due to the capture of tissue T between anvil 24 and staple cartridge 22. This has been found not to affect the efficacy of staples applied to tissue T and crimped in anvil 24. As such, it is not critical to the stapling of tissue T to exactly orient staple cartridge 22 relative to elongate tubular member 14.

Figure 8:
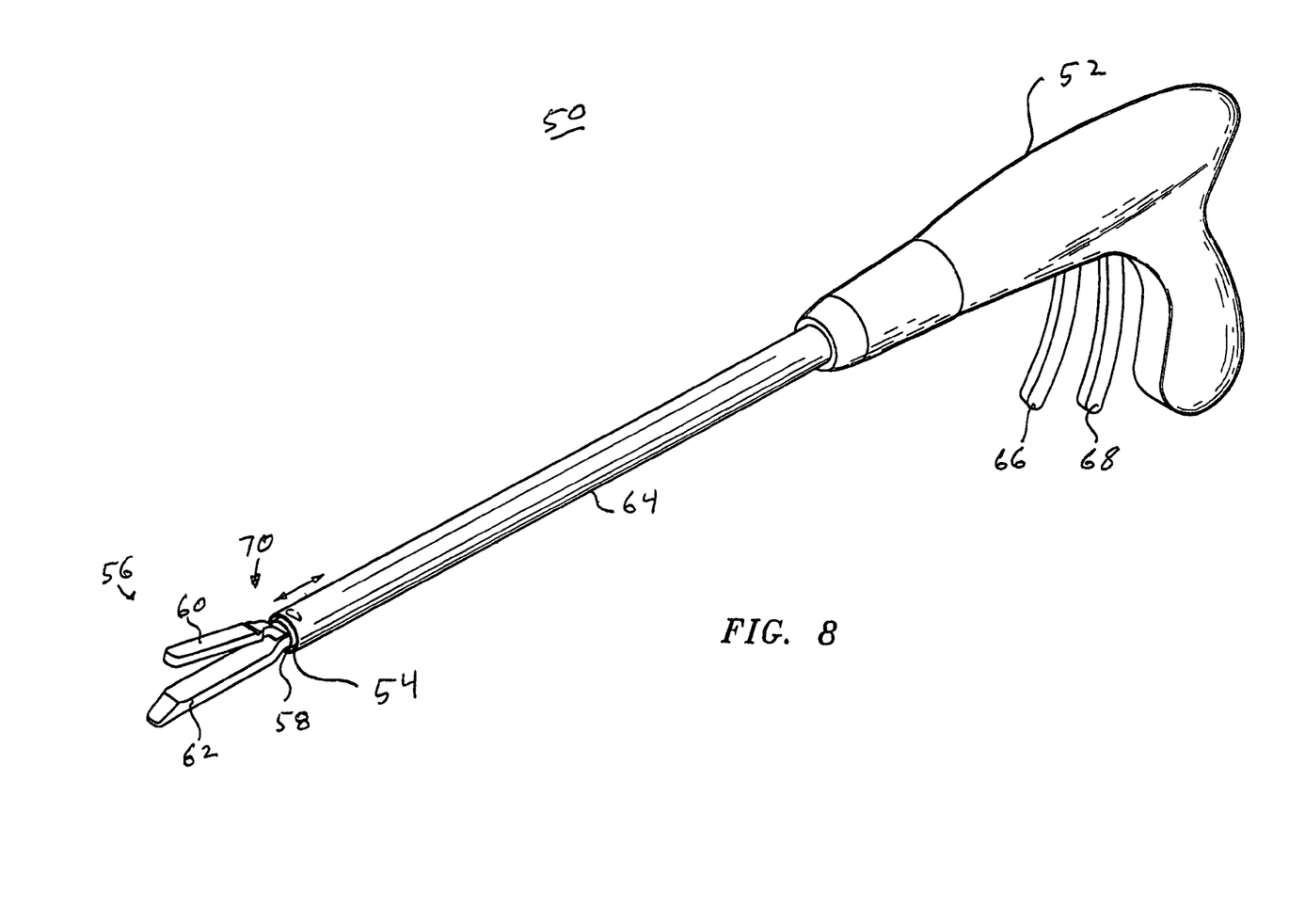
FIG. 8 is a perspective view of a surgical stapler incorporating an alternative embodiment of an anvil position detector.

Referring now to FIG. 8, there is disclosed an alternative surgical stapler 50 incorporating an alternative mechanism for indicating the proper position of an anvil associated with surgical stapler 50. Surgical stapler 50 generally includes a handle 52 having an inner member 54 extending distally from handle 52. A jaw assembly 56 is mounted on a distal end 58 of inner member 54. Jaw assembly 56 includes an anvil 60 and a staple cartridge 62. An outer tubular member 64 is mounted for longitudinal movement relative to inner member 54 and handle 52. Outer tubular member 64 is provided to cam anvil 60 from an open position spaced apart from staple cartridge 62 to a closed position substantially adjacent to staple cartridge 62. A first trigger 66 is movably mounted on handle 52 and operates to move outer tubular member 64 longitudinally relative to inner member 54. A second trigger 68 is provided to eject staples (not shown) from staple cartridge 62 and into anvil 60 in order to staple tissue captured there between. As noted hereinabove, surgical stapler 50 incorporates an alternative anvil position detector 70 for providing an indication to the operator of surgical stapler 50 when anvil 60 has been properly oriented relative to the remainder of surgical stapler 50.

Figure 9:
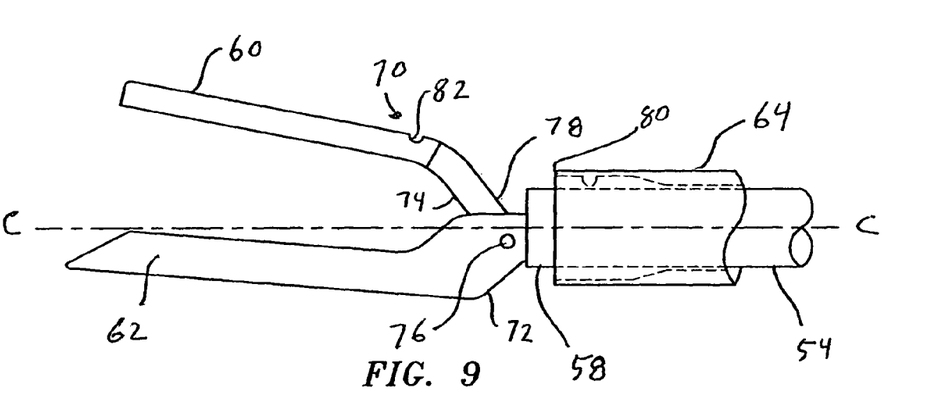
FIG. 9 is a side elevation view of the distal end of the surgical stapler of FIG. 8.

As best shown in FIG. 9, a proximal end 72 of staple cartridge 62 is affixed to distal end 58 of inner member 54. Anvil 60 is movably mounted with respect to staple cartridge 62. A proximal end 74 of anvil 60 is pivotally mounted to staple cartridge 62 at pivot 76. In order to move anvil 60 between the open and closed positions, anvil 60 includes an angled edge 78 at proximal end 74 of anvil 60. Outer tubular member 64 is provided with a distal or camming edge 80 which is configured to engage angled edge 78 to move anvil 60 from the open to the closed position. As noted hereinabove, surgical stapler 50 includes an anvil position detector 70 to give the operator an indication of the proper positioning of anvil 60. Similar to anvil 24 described hereinabove, anvil 60 includes a cross notch 82.

Figure 10:
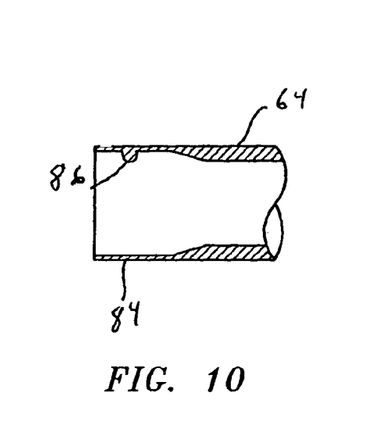
FIG. 10 is a cross-sectional view of the distal end of a drive tube of the surgical stapler of FIG. 8 incorporating part of the anvil position detector.

Referring for the moment to FIG. 10, and as noted hereinabove, outer tubular member 64 is hollow for movement over inner member 54. Outer tubular member 64 includes a distal end 84 and an inwardly directed projection 86, which forms part of anvil position detector 70, and which is configured to engage cross notch 82 in anvil 60 (FIG. 9).

Figure 11:
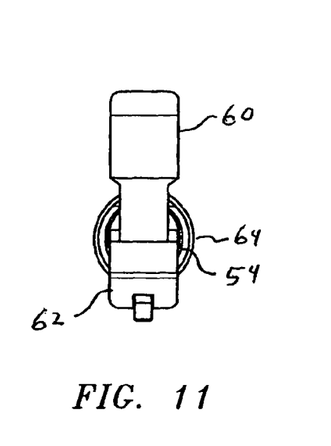
FIG. 11 is an end view of the distal end of the surgical stapler of FIG. 8.
Figure 12:
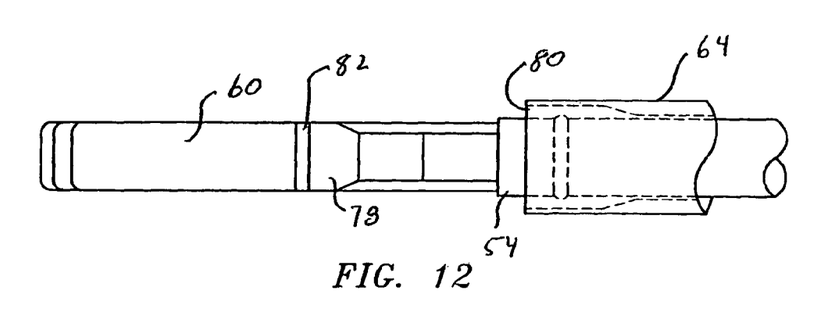
FIG. 12 is a top view of the distal end of the surgical stapler of FIG. 8.
Figure 13:
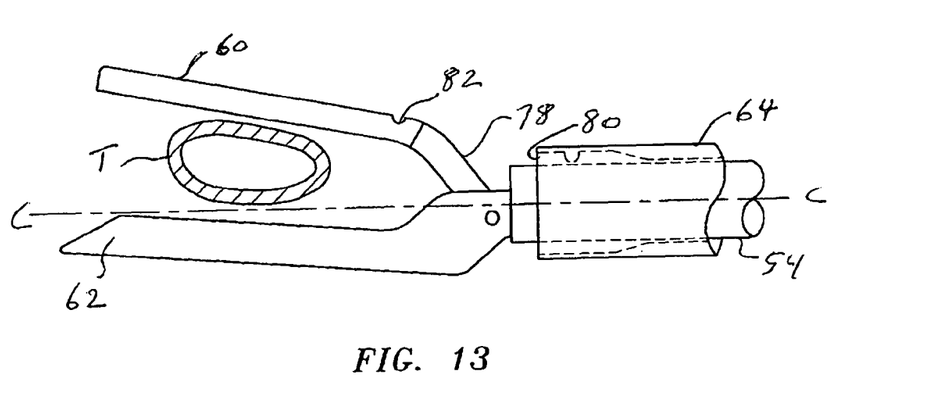
FIG. 13 is a side view of the distal end of the surgical stapler of FIG. 8 positioned about tissue.
Figure 14:
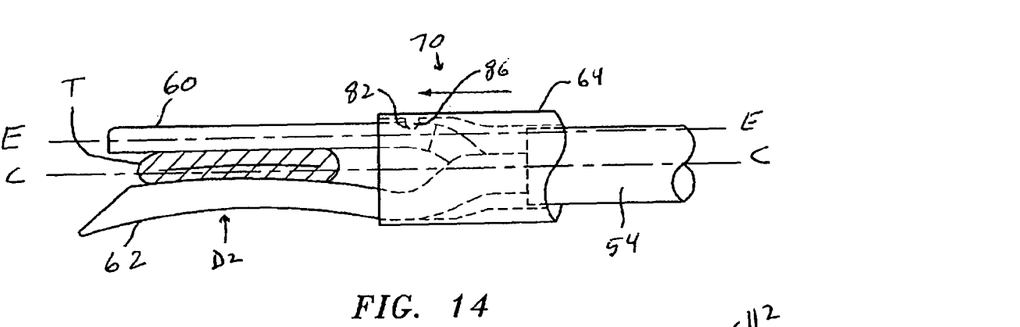
FIG. 14 is a side elevation view of the distal end of the surgical stapler of FIG. 8 with the tissue captured between the jaws and the anvil position detector engaged.

Referring now to FIGS. 11 and 12, in the initial position, anvil 60 is in the open position spaced apart from staple cartridge 62 (FIG. 11). Outer tubular member 64, including camming edge 80, is in a proximal position relative to angled edge 78 on anvil 60 (FIG. 12). As best shown in FIG. 13, anvil 60 and staple cartridge 62 are initially positioned about a tubular tissue section T. Actuation of first trigger 66 (FIG. 8) causes outer tubular member 64 to move distally forcing camming edge 80 into engagement with angled edge 78. Engagement of camming edge 80 with angled edge 78 moves anvil 60 from the open position to the closed position relative to staple cartridge 62 as best shown in FIG. 14. As with surgical stapler 10 described hereinabove, engagement of anvil position detector 70, including cross notch 82 and inward projection 86, is configured to correspond to the condition where a longitudinal axis E-E of anvil six the is in the proper orientation, i.e. approximately parallel to, a longitudinal axis C-C of inner member 54. As inward projection 86 on outer tubular the member 64 engages cross notch 82 in anvil 60, the user is provided with an audible and tactile indication that anvil 60 is in proper alignment with respect to the remainder of surgical stapler 50. As shown, and as noted hereinabove, a certain amount of deflection D2 may occur in staple cartridge 62 without affecting the ability of anvil 62 properly crimps staples about tissue section T.

Figures 15, 16:
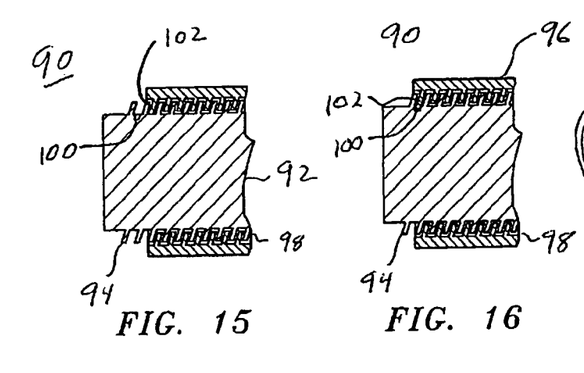
FIG. 15 is a cross-sectional view of an alternate embodiment of an anvil position detector for use with the jaw closure mechanism of a surgical stapler.
FIG. 16 is a cross-sectional view of the anvil position detector of FIG. 15 in the engaged position.

Referring now to FIGS. 15 and 16, there is disclosed a further alternative embodiment of an anvil position indicator 90. Anvil position indicator 90 is configured for use with an anvil closure mechanism that incorporates interengaging threaded members such as, for example, a jackscrew etc. An inner member 92 includes threads 94 and a hollow outer member 96 includes corresponding threads 98. Inner member 92 is provided with a notch 100 which is formed as an enlarged or deepened area in threads 94. Similarly, outer member 96 includes an enlarged projection on inner threads 98 which is configured to engage notch 100. As with prior embodiments, engagement of projection 102 with notch 100 corresponds to the condition where a jaw and handle of a surgical instrument are in proper orientation for use. Likewise, similar to that disclosed hereinabove, engagement of projection 102 with notch 100 provides both an audible and tactile indication to the user that the proper alignment has been obtained.

Figure 17:
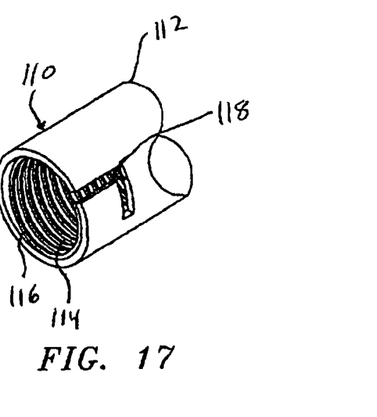
FIG. 17 is a perspective view of the distal end of a component of an anvil position detector.

Referring finally to FIG. 17, there is illustrated a distal end 110 of a hollow outer member 112. As with outer member 96 above, inner threads 114 include an enlarged projection or enlarged distal most thread 116. Distal end 110 of outer member 112 includes an L-shaped cutout 118 which allows distal end 110 to flex or act as a sprung member preventing enlarged distal most thread 116 from jamming with threads on a corresponding inner member until enlarged distal most thread 116 drops into a corresponding notch in the inner member.

While the above described anvil position indicator mechanisms have been disclosed as giving audible, and/or, tactile indications to the user of the proper alignment of a jaw associated with a surgical instrument, it is also within the contemplated scope of the invention to provide an audible or visual signal via electrical means to the user. This can be accomplished by a electrically insulating the disclosed March from the remainder of the anvil material and electrically insulating the disclosed projection from the remainder of the drive mechanism used to close the anvil member. The notch and projection may form contacts which, when engaged, provide an electrical signal to indicator mechanism 5 (FIG. 1) associated with a surgical instrument which in turn can provide a visual and/or audible indication to the user that the notch of projection have been properly engaged. In the alternative, a simple contact switch can be used.

It will be understood that various modifications may be made to the embodiments disclosed herein. For example, the materials used in the engaging components may be the same materials or dissimilar materials so as to enhance the audible and tactile signals given to the user. Further, the engagement of a projection into a notch may be provided in other jaw closure mechanism so as to give the and operator of an audible and tactile indication of proper functioning of the surgical instrument. Additionally, the disclosed and the position detectors may be used in other jaw structures such as, for example, tissue graspers, tissue cutters, clip appliers, etc. Therefore, the above description should not be construed as limiting, but merely as exemplifications of particular embodiments. Those skilled in the art will envision other modifications within the scope and spirit of the claims appended hereto.

The invention claimed is:

1. A surgical instrument incorporating a jaw position detector comprising:

a support member having a first longitudinal axis;

a jaw movably mounted on the support member and having a second longitudinal axis, the jaw including a tissue engaging surface and an outer surface disposed in a directly opposite relation to the tissue engaging surface, the outer surface defining a proximal portion and a distal portion, the proximal portion being disposed at an angle relative to the first longitudinal axis of the support member, the distal portion being disposed parallel to the first longitudinal axis of the support member when the jaw is in a closed position;

a drive mechanism associated with the support member and operable to move the jaw relative to the support member as the drive mechanism translates between proximal and distal positions; and a position detector including a notch formed on a proximal region of the distal portion of the outer surface, a projection mounted to the drive mechanism, and a indicator mechanism electrically coupled to the notch and the projection, wherein the projection is configured and dimensioned to move along the jaw with respect to the first longitudinal axis as the jaw moves from an open position to the closed position to provide an indication to an operator of the surgical instrument when the first longitudinal axis is in substantial alignment with the second longitudinal axis, wherein the projection snaps into the notch after the jaw is in the closed position to fix the jaw in the closed position, wherein the projection is located in the notch when the drive mechanism is in the distal position, and wherein when the notch and projection are engaged, the indictor mechanism provides an indication to the user or operator that the jaw and the drive mechanism are properly engaged.

2. The surgical instrument as recited in claim 1, wherein the support member is an elongate tubular member and the drive mechanism includes a driver movable within the elongate tubular member.

3. The surgical instrument as recited in claim 2, wherein the projection is disposed in mechanical cooperation with the driver and is a cross pin oriented transverse to the driver.

4. The surgical instrument as recited in claim 1, wherein the notch is transverse to the second longitudinal axis.

5. The surgical instrument as recited in claim 1, wherein an engagement of the projection with the notch provides a tactile indication to the user or operator.

6. The surgical instrument as recited in claim 1, wherein an engagement of the projection with the notch provides an audible indication to the user or operator.

7. The surgical instrument as recited in claim 1, wherein the projection moves along the first longitudinal axis in response to actuation of the drive mechanism.

8. The surgical instrument as recited in claim 1, wherein the jaw is positioned at an acute angle relative to the support member in the open position and is substantially parallel with the support member in the closed position.

9. The surgical instrument as recited in claim 1, wherein the first longitudinal axis and the second longitudinal axis are disposed at an acute angle in the open position and are substantially parallel in the closed position.

10. The surgical instrument as recited in claim 1, wherein the projection moves substantially longitudinally along the outer surface of the jaw.

11. The surgical instrument as recited in claim 1, wherein the projection and the notch have an arcuate shape with a substantially similarly dimensioned radii such that the arcuate shapes of the projection and the notch are complementary.

12. The surgical instrument according to claim 1, further comprising an actuator operably coupled to the drive mechanism, the drive mechanism moving the projection from a disengaged position to an engaged position relative to the jaw upon the actuation of the actuator.

13. The surgical instrument according to claim 1, wherein the notch is the sole opening in the outer surface of the jaw.

14. A surgical instrument incorporating a jaw position detector comprising:

a support member having a first longitudinal axis;

a jaw movably mounted on the support member and having a second longitudinal axis, the jaw including a tissue engaging surface and an outer surface disposed in a directly opposite relation to the tissue engaging surface, the outer surface defining a first portion and a second portion, the first portion being disposed at an angle relative to the first longitudinal axis of the support member, the second portion being disposed parallel to the first longitudinal axis of the support member when the jaw is in a closed position;

a drive mechanism movable over the support member and operable to move the jaw relative to the support member as the drive mechanism translates between proximal and distal positions; and a position detector including a notch formed on a proximal portion of the second portion of the outer surface, a projection extending from the drive mechanism, and a indicator mechanism electrically coupled to the notch and the projection, wherein the projection moves along the jaw with respect to the first longitudinal axis upon the movement of the jaw from an open position to the closed position to provide an indication to an operator of the surgical instrument when the first longitudinal axis is in substantial alignment with the second longitudinal axis, wherein the projection snaps into the notch after the jaw is in the closed position to fix the jaw in the closed position, wherein the projection is located in the notch when the drive mechanism is in the distal position, wherein when the notch and projection are engaged, the indictor mechanism provides an indication to the user or operator that the jaw and the drive mechanism are properly engaged.

15. The surgical instrument as recited in claim 14, wherein the drive mechanism includes an outer tubular member movable over the support member and engageable with the jaw to move the jaw relative to the support member.

16. The surgical instrument as recited in claim 15, wherein the projection is disposed in mechanical cooperation with the outer tubular member and is inwardly directed.

17. The surgical instrument as recited in claim 15, wherein an engagement of the projection in the outer tubular member with the notch formed in the jaw provides a tactile indication to the user or operator.

18. The surgical instrument as recited in claim 15, wherein an engagement of the projection in the outer tubular member with the notch formed in the jaw provides an audible indication to the user or operator.

19. The surgical instrument as recited in claim 14, wherein the notch is transverse to the second longitudinal axis.

* * * * *